US012629917B2

(12) United States Patent
Zhang et al.

(10) Patent No.: US 12,629,917 B2
(45) Date of Patent: May 19, 2026

---

(54) SINGLE SIDED HYDROPHILIC NONWOVEN FABRIC WITH HIGH TENSIBLE STRENGTH AND CSR WRAP MADE THEREFROM

(71) Applicant: Berry Global, Inc., Evansville, IN (US)

(72) Inventors: Tianlei Zhang, Weifang (CN); Dong Wu, Suzhou (CN); Yongji Jin, Shanghai (CN); Fang Guo, Suzhou (CN)

(73) Assignee: MAGNERA CORPORATION, Charlotte, NC (US)

( * ) Notice: Subject to any disclaimer, the term of this patent is extended or adjusted under 35 U.S.C. 154(b) by 148 days.

(21) Appl. No.: 18/368,254

(22) Filed: Sep. 14, 2023

(65) Prior Publication Data

US 2024/0092059 A1 Mar. 21, 2024

(30) Foreign Application Priority Data

Sep. 15, 2022 (CN) .......................... 202211121032.8

(51) Int. Cl.
B32B 5/26 (2006.01)
A61L 2/07 (2006.01)
(Continued)

(52) U.S. Cl.
CPC ............... B32B 5/269 (2021.05); A61L 2/07 (2013.01); A61L 2/26 (2013.01); B32B 5/022 (2013.01);
(Continued)

(58) Field of Classification Search
CPC ..... B32B 5/269; B32B 5/022; B32B 2250/04;

B32B 2250/20; B32B 2250/40; B32B 2262/0253; B32B 2307/54; B32B 2307/728; B32B 2307/73; B32B 2439/80; A61L 2/07; A61L 2/26; A61L 2202/181; A61L 2202/24; B65D 65/40;
(Continued)

(56) References Cited

U.S. PATENT DOCUMENTS

| | | | |
|---|---|---|---|
| 2002/0142692 A1* | 10/2002 | Ferencz | ................. D04H 1/559 2/51 |
| 2011/0217894 A1 | 9/2011 | Coslett et al. | |

(Continued)

FOREIGN PATENT DOCUMENTS

| | | |
|---|---|---|
| CN | 103696147 A | 4/2014 |
| CN | 111516329 A | 8/2020 |

OTHER PUBLICATIONS

International Search Report and Written Opinion issued in corresponding International Application No. PCT/US2023/032815, all enclosed pages cited.

(Continued)

*Primary Examiner* — Jeremy R Pierce
(74) *Attorney, Agent, or Firm* — BURR & FORMAN

(57) ABSTRACT

The present application discloses a single sided hydrophilic nonwoven fabric with high tensile strength and a CSR wrap made therefrom, wherein the single sided hydrophilic nonwoven fabric has a spunbonded/meltblown/spunbonded (SMS) structure consisting of a top spunbonded layer, a middle meltblown layer and a bottom spunbonded layer, wherein one side of the nonwoven fabric is hydrophilic, and the other side of the nonwoven fabric is hydrophobic.

18 Claims, 2 Drawing Sheets

Top spunbonded layer

Middle meltblown layer

Bottom spunbonded layer

(51) Int. Cl.

| | |
|---|---|
| *A61L 2/26* | (2006.01) |
| *B32B 5/02* | (2006.01) |
| *B65B 11/00* | (2006.01) |
| *B65B 55/02* | (2006.01) |
| *B65D 65/40* | (2006.01) |
| *D04H 1/4291* | (2012.01) |
| *D04H 1/44* | (2006.01) |
| *D04H 1/559* | (2012.01) |
| *D04H 1/56* | (2006.01) |
| *D04H 3/16* | (2006.01) |
| *D06M 13/224* | (2006.01) |
| *A61L 103/15* | (2026.01) |
| *D06M 101/20* | (2006.01) |

(52) U.S. Cl.

CPC ............ *B65B 11/004* (2013.01); *B65B 55/02* (2013.01); *B65D 65/40* (2013.01); *D04H 1/4291* (2013.01); *D04H 1/44* (2013.01); *D04H 1/559* (2013.01); *D04H 1/56* (2013.01); *D04H 3/16* (2013.01); *D06M 13/2243* (2013.01); *A61L 2103/15* (2026.01); *A61L 2202/181* (2013.01); *B32B 2250/04* (2013.01); *B32B 2250/20* (2013.01); *B32B 2250/40* (2013.01); *B32B 2262/0253* (2013.01); *B32B 2307/54* (2013.01); *B32B 2307/728* (2013.01); *B32B 2307/73* (2013.01); *B32B 2439/80* (2013.01); *D06M 2101/20* (2013.01); *D06M 2200/00* (2013.01); *D10B 2321/022* (2013.01); *D10B 2401/021* (2013.01); *D10B 2401/022* (2013.01); *D10B 2401/063* (2013.01); *D10B 2403/011* (2013.01); *D10B 2505/10* (2013.01); *D10B 2509/00* (2013.01)

(58) Field of Classification Search

CPC ........ D04H 1/4291; D04H 1/44; D04H 1/559; D04H 1/56; D04H 3/16; D06M 13/2243; D06M 2101/20; D06M 2200/00; D10B 2401/021; D10B 2401/022; D10B 2401/063; D10B 2403/011; D10B 2505/10; D10B 2509/00

See application file for complete search history.

(56) References Cited

U.S. PATENT DOCUMENTS

| | | | | |
|---|---|---|---|---|
| 2012/0108714 A1* | 5/2012 | Wittner | .................. | D04H 3/007 |
| | | | | 524/226 |
| 2012/0177888 A1* | 7/2012 | Escafere | ............... | D04H 1/559 |
| | | | | 28/100 |
| 2019/0284739 A1* | 9/2019 | Wang | .................... | D04H 1/559 |

OTHER PUBLICATIONS

International Preliminary Report on Patentability issued in corresponding International Application No. PCT/US2023/032815 mailed Nov. 28, 2024, all pages cited in its entirety.

Second Written Opinion issued on Jul. 31, 2024 in corresponding International Application No. PCT/US2023/032815, all enclosed pages cited.

Non-Final Office Action from corresponding Thailandese Application No. 2501001634, mailed Jun. 27, 2025, all pages cited in its entirety.

* cited by examiner

SINGLE SIDED HYDROPHILIC NONWOVEN FABRIC WITH HIGH TENSIBLE STRENGTH AND CSR WRAP MADE THEREFROM

CROSS REFERENCE TO RELATED APPLICATIONS

This application claims the benefit of Chinese Priority application No. 202211121032.8 filed Sep. 15, 2022, the contents of which are incorporated herein by reference in their entirety.

TECHNICAL FIELD

The present application relates to a single sided hydrophilic nonwoven fabric with high tensile strength and a central supply room (CSR) wrap made therefrom.

BACKGROUND ART

It is usually necessary to wrap medical devices or equipment before sterilization in the surgical supply room or CSR of a hospital. These medical devices or equipment are usually wrapped using CSR wrap to be protected during sterilization and maintain their sterility during later storage.

Existing CSR wrap is typically made from a spunbonded/meltblown/spunbonded (SMS) non-woven fabric which is tear-resistant and easy to fold. The non-woven fabric is a non-woven wrapping fabric composed of a spunbonded layer, a meltblown layer and a spunbonded layer. As a wrapping material for sterilization, CSR wrap should meet the following requirements: it should repel water, blood and saline, making it possible to effectively prevent the penetration of airborne bacteria and aquatic bacteria to provide a sterile barrier system; it should have sufficient functional strength and durability during the treatment and use; and it should be designed to be highly air permeable to prevent wet packs, while having high bacterial filterability. In addition, the CSR wrap made from a SMS non-woven fabric is usually sterilized via steam sterilization method in autoclaves. The problems of wet packs and damaged (holes, tears, cracks, etc.) packs occur frequently due to various reasons such as low permeability of materials in the wrap, high loading capacity, and sharp medical devices, and the like, and both wet packs and damaged packs will lead to the failure of sterile barrier system.

Therefore, there is a need to develop non-woven fabrics and CSR wrap that have excellent antimicrobial properties while effectively preventing wet packs and damaged packs.

SUMMARY OF INVENTION

In view of the above problems, it is an object of the present application to provide a single sided hydrophilic nonwoven fabric with high tensile strength.

Another object of the present application is to provide a CSR wrap made from the single sided hydrophilic nonwoven fabric.

According to one aspect of the present application, there is provided a single sided hydrophilic nonwoven fabric which has a spunbonded/meltblown/spunbonded (SMS) structure consisting of a top spunbonded layer, a middle meltblown layer and a bottom spunbonded layer, wherein one side of the nonwoven fabric is hydrophilic, and the other side of the nonwoven fabric is hydrophobic.

In one embodiment, the single sided hydrophilic nonwoven fabric may have a basis weight of from 20 gsm to 150 gsm.

In one embodiment, the raw materials for forming each of the layers of the single sided hydrophilic nonwoven fabric may comprise polypropylene resin. Wherein, the Melt Flow Rate (MFR) of the polypropylene resin for forming the middle meltblown layer may be between 800 g/10 min and 1800 g/10 min, especially 1400 g/10 min. In addition, the Melt Flow Rate of polypropylene resin for forming the top spunbonded layer and the bottom spunbonded layer may be between 35 g/10 min and 40 g/10 min.

In one embodiment, the raw materials for forming each of the layers of the single sided hydrophilic nonwoven fabric may further comprise a color masterbatch. The color masterbatch may be white, yellow, blue, green, purple, pink, etc.

In one embodiment, a color masterbatch may be added to the middle meltblown layer and the bottom spunbonded layer. The color masterbatch may be added in an amount of from 1 wt % to 10 wt %, based on the total weight of the middle meltblown layer. In addition, the color masterbatch may be added in an amount of from 1 wt % to 10 wt %, based on the total weight of the bottom spunbonded layer.

According to one embodiment of the present application, each of the top spunbonded layer and the bottom spunbonded layer may be composed of one or more spunbonded layers. According to one embodiment of the present application, the middle meltblown layer may be composed of one or more meltblown layers, for example, two meltblown layers.

The single sided hydrophilic nonwoven fabric according to the present application has high tensile strength to accommodate or wrap medical devices, so that it is not easy to be damaged or torn during processing or use, thus effectively preventing the occurrence of damaged packs.

In one embodiment, the single sided hydrophilic nonwoven fabric may have 60 wt % to 95 wt % of spunbonded fibers to provide sufficient tensile strength.

In one embodiment, a tensile enhancer may be added to the top spunbonded layer and the bottom spunbonded layer to further improve the tensile strength of the single sided hydrophilic nonwoven fabric.

In one embodiment, the tensile enhancer may be added in an amount of from 1 wt % to 10 wt %, based on the total weight of each of the spunbonded layers.

In one embodiment, the tensile strengths of the single sided hydrophilic nonwoven fabric in the longitudinal direction (i.e., machine direction, MD) and the transverse direction (i.e., cross direction, CD), as determined in accordance with EN ISO 1924-2, may be in the range of 1.2 KN/m to 5.0 KN/m, respectively.

In one embodiment, the longitudinal tensile strength of the single sided hydrophilic nonwoven fabric, as determined in accordance with EN ISO 1924-2, may be in the range of 2 KN/m to 5.0 KN/m.

In one embodiment, the longitudinal elongation of the single sided hydrophilic nonwoven fabric, as determined in accordance with EN ISO 1924-2, may be in the range of 50% to 120%.

In one embodiment, the transverse tensile strength of the single sided hydrophilic nonwoven fabric, as determined in accordance with EN ISO 1924-2, may be in the range of 1.5 KN/m to 3.5 KN/m.

In one embodiment, the transverse elongation of the single sided hydrophilic nonwoven fabric, as determined in accordance with EN ISO 1924-2, may be in the range of 50% to 150%.

One side of the single sided hydrophilic nonwoven fabric according to the present application is hydrophilic, so that the condensed water may be absorbed after steam sterilization. In addition, the other side of the single sided hydrophilic nonwoven fabric is hydrophobic, so that the penetration of moisture may be prevented during steam sterilization or during storage. Therefore, when the single sided hydrophilic nonwoven fabric of the present application is used as the CSR wrap, the occurrence of wet packs may be effectively prevented.

According to one embodiment of the present application, the single sided hydrophilic nonwoven fabric has at least two spunbonded layers, wherein at least one of the spunbonded layers is a hydrophilic spunbonded layer and at least one of the spunbonded layers is a hydrophobic spunbonded layer.

In the single sided hydrophilic nonwoven fabric according to one embodiment, the top spunbonded layer may be a hydrophilic spunbonded layer and the bottom spunbonded layer may be a hydrophobic spunbonded layer. In another embodiment, the top spunbonded layer may be a hydrophobic spunbonded layer and the bottom spunbonded layer may be a hydrophilic spunbonded layer.

In one embodiment, the hydrophilic spunbonded layer may account for 30% to 50% of the weight of the whole single sided hydrophilic nonwoven fabric. The diameter of the fibers in the hydrophilic spunbonded layer may preferably be between 15 µm and 25 µm, and the average diameter of the fibers may be about 19 µm.

In one embodiment, the hydrophobic spunbonded layer may account for 30% to 50% of the weight of the whole single sided hydrophilic nonwoven fabric. The diameter of the fibers in the hydrophobic spunbonded layer may preferably be between 15 µm and 25 µm, and the average diameter of the fibers may be 19 µm.

In one embodiment, a hydrophilic masterbatch may be added to the top spunbonded layer, in order to make the top spunbonded layer hydrophilic. In one embodiment, the hydrophilic masterbatch may be a glyceride of fatty acids.

In one embodiment, the hydrophilic masterbatch may be added in an amount of from 1 wt % to 10 wt %, based on the total weight of the hydrophilic spunbonded layer.

In one embodiment, the water absorption capacity of the single sided hydrophilic nonwoven fabric, as determined in accordance with GB/T 1540 method, may be between 10 $g/m^2$ and 30 $g/m^2$.

The single sided hydrophilic nonwoven fabric according to the present application has excellent antimicrobial properties, and when it is designed and manufactured for CSR wrap application, the microbial barrier as determined in accordance with EN868 can be maintained for 180 days or longer.

In one embodiment, the single sided hydrophilic nonwoven fabric may have 5 wt % to 40 wt % of meltblown fibers, which will provide high barrier properties to prevent the penetration of microorganisms and bacteria. In another embodiment, the middle meltblown layer may account for 10 wt % to 30 wt % of the weight of the whole single sided hydrophilic nonwoven fabric.

In particular, the diameter of the fibers in the middle meltblown layer may be between 0.5 µm and 10 µm, and the average diameter of the fibers may be about 2 µm.

According to another aspect of the present application, there is provided a CSR wrap made from the above single sided hydrophilic nonwoven fabric, wherein the hydrophilic spunbonded layer serves as the inner layer of the CSR wrap, and the hydrophobic spunbonded layer serves as the outer layer of the CSR wrap.

As the single sided hydrophilic nonwoven fabric of the present application can provide sufficient tensile strength, it is not easy to be damaged when making CSR wrap to accommodate medical devices, thus effectively preventing the occurrence of damaged packs. In addition, one side of the single sided hydrophilic nonwoven fabric of the present application is a hydrophilic spunbonded layer, which can absorb the condensed water after steam sterilization; and the other side thereof is a hydrophobic spunbonded layer, which can prevent the penetration of moisture during steam sterilization or during storage, thereby effectively preventing the occurrence of wet packs. In addition, the hydrophobic meltblown layer and the hydrophobic bottom spunbonded layer provide a sterile barrier, thus effectively preventing the penetration of bacteria. Therefore, the single sided hydrophilic nonwoven fabric and CSR wrap according to the present application can have excellent antimicrobial properties, while effectively preventing the occurrence of wet packs and damaged packs.

BRIEF DESCRIPTION OF DRAWINGS

The following drawings attached to the specification illustrate preferred embodiments of the present application by way of examples, and are used in conjunction with the detailed description of the present application given below to enable the technical concepts of the present application to be further understood, and therefore, the contents of such drawings should not be used alone to explain the present application.

DETAILED DESCRIPTION

Figure 1:
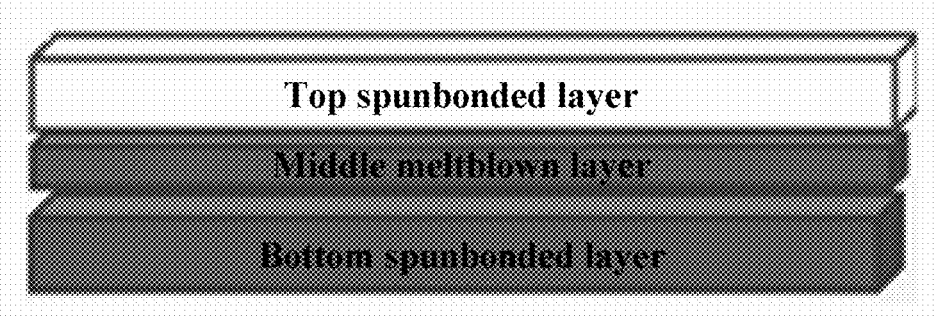
FIG. 1 is a schematic view of the single sided hydrophilic nonwoven fabric according to a preferred embodiment of the present application.

Hereinafter, various embodiments of the present application will be described in detail with reference to the drawings. However, the present application may be implemented in many different forms and should not be construed to be limited to the embodiments set forth herein.

The terminology used herein is for the purpose of describing specific exemplary embodiments only, and is not intended to be limiting. The singular forms "a", "an" and "the" as used herein may be intended to include the plural forms as well, unless clearly indicated otherwise in the context. The terms "comprise(s)", "contain(s)"", "include(s)"" and "have/has" are inclusive, thus specifying the presence of the stated features, integers, steps, operations, elements and/or components, but not excluding the presence or addition of one or more other features, integers, steps, operations, elements, components and/or groups thereof. The method steps, processes and operations described herein should not be interpreted as necessarily requiring them performing in the particular order discussed or illustrated, unless specifically identified as an order of performing. It should also be understood that additional or alternative steps may be taken.

The single sided hydrophilic nonwoven fabric in the present application refers to a nonwoven fabric with spunbonded/meltblown/spunbonded (SMS) structure, where S represents single or multiple spunbonded beam(s), and M represents single or multiple meltblown beam(s). The single sided hydrophilic nonwoven fabric of the present application is a laminate composed of a top spunbonded layer, a middle meltblown layer and a bottom spunbonded layer, wherein any one of the top spunbonded layer, the middle meltblown layer and the bottom spunbonded layer may be composed of one or more layers. Therefore, the term "SMS structure" used in the meaning of the present application not only means an "S-M-S' laminate composed of a spunbonded layer, a meltblown layer and another spunbonded layer, but also may mean a laminate with structures such as "S-S-M-S", "S-M-M-S", and "S-M-S-S", etc. For example, in one embodiment, the middle meltblown layer may be composed of two layers.

In one embodiment, the single sided hydrophilic nonwoven fabric may have a basis weight of from 20 gsm to 100 gsm, preferably from 40 gsm to 80 gsm, and more preferably from 50 gsm to 70 gsm.

In the present application, the raw material for each of the spunbonded layers and the middle meltblown layer of single sided hydrophilic nonwoven fabric may comprise a polyethylene homopolymer or a copolymer thereof, or a polypropylene homopolymer or a copolymer thereof, and polypropylene resin is particularly preferred. Polypropylene resin is widely used in the manufacture of non-woven fabrics with SMS structure.

The melt flow rate of polypropylene resin suitable for the middle meltblown layer in the present application may be between 800 g/10 min and 1800 g/10 min, preferably between 1200 g/10 min and 1600 g/10 min, especially about 1400 g/10 min.

The melt flow rate of polypropylene resin suitable for each of the spunbonded layers in the present application may be between 35 g/10 min and 40 g/10 min, for example, about 35 g/10 min.

In addition, during the formation of the middle meltblown layer and each of the spunbonded layers, color masterbatches of various colors, such as white, yellow, blue, green, purple, pink, etc., can also be added, in order to allow the single sided hydrophilic nonwoven fabric of the present application to be colored.

In one embodiment, a color masterbatch may be added to the middle meltblown layer and the bottom spunbonded layer. The color masterbatch may be added in an amount of from 1 wt % to 10 wt %, and preferably from 1.5 wt % to 8 wt %, based on the total weight of the middle meltblown layer. Additionally, the color masterbatch may be added in an amount of from 1 wt % to 10 wt %, and preferably from 1.5 wt % to 8 wt %, based on the total weight of the bottom spunbonded layer.

The single sided hydrophilic nonwoven fabric according to the present application has high tensile strength and/or elongation. High tensile strength and/or elongation make the single sided hydrophilic non-woven fabric not easy to be damaged when accommodating or wrapping medical devices, thus effectively preventing the occurrence of damaged packs.

According to one aspect of the present application, the single sided hydrophilic nonwoven fabric may include 60 wt % to 95 wt % of spunbonded fibers, which may provide sufficient tensile strength. Preferably, the single sided hydrophilic nonwoven fabric may include spunbonded fibers ranging from 70 wt % to 90 wt %, and more preferably ranging from 75 wt % to 85 wt %. When the content of the spunbonded fibers in the single sided hydrophilic nonwoven fabric is less than 60 wt %, the tensile strength of the nonwoven fabric may be insufficient, and when the content of spunbonded fibers is higher than 95%, the sterile barrier performance may be unfavorably decreased.

In addition, a tensile enhancer may be added to the top spunbonded layer and/or the bottom spunbonded layer to further improve the tensile strength of the single sided hydrophilic nonwoven fabric. In one embodiment, a tensile enhancer may be added to both the top spunbonded layer and the bottom spunbonded layer.

In the present application, the types of the tensile enhancer are not limited, as long as it is a material that can increase the crystallization percentage of spunbonded materials. The tensile enhancer may be added in an amount of between 1 wt % and 10 wt %, preferably between 1 wt % and 8 wt %, and more preferably between 2 wt % and 5 wt %, based on the total weight of each of the spunbonded layers.

In one embodiment, the tensile strengths of the single sided hydrophilic nonwoven fabric in the longitudinal direction (i.e., machine direction, MD) and the transverse direction (i.e., cross direction, CD), as determined in accordance with EN ISO 1924-2, may each be in the range of 1.2 KN/m to 5.0 KN/m.

In one embodiment, the longitudinal tensile strength of the single sided hydrophilic nonwoven fabric, as determined in accordance with EN ISO 1924-2, may be in the range of 2 KN/m to 5.0 KN/m, for example, in the range of 2.5 KN/m to 4.0 KN/m.

In one embodiment, the longitudinal elongation of the single sided hydrophilic nonwoven fabric, as determined in accordance with EN ISO 1924-2, may be in the range of 50% to 120%, for example, in the range of 70% to 100%.

In one embodiment, the transverse tensile strength of the single sided hydrophilic nonwoven fabric, as determined in accordance with EN ISO 1924-2, may be in the range of 1.5 KN/m to 3.5 KN/m, for example, in the range of 1.6 KN/m to 3.0 KN/m.

In one embodiment, the transverse elongation of the single sided hydrophilic nonwoven fabric, as determined in accordance with EN ISO 1924-2, may be in the range of 50% to 150%, for example, in the range of 70% to 100%.

In an embodiment according to the present application, the single sided hydrophilic nonwoven fabric has at least two spunbonded layers, wherein at least one of the spunbonded layers is a hydrophilic spunbonded layer so as to absorb the condensed water after steam sterilization, and at least one of the spunbonded layers is a hydrophobic spunbonded layer so as to provide a barrier to prevent the penetration of bacteria. Therefore, when the single sided hydrophilic nonwoven fabric of the present application is used as a CSR wrap, the occurrence of wet packs can be effectively prevented.

In one embodiment according to the present application, one spunbonded layer of the single sided hydrophilic nonwoven fabric is designed to be hydrophilic. In one embodiment, only the top spunbonded layer in the single sided hydrophilic nonwoven fabric is designed to be a hydrophilic spunbonded layer, and the bottom spunbonded layer is designed to be a hydrophobic spunbonded layer. When the top spunbonded layer is composed of two or more layers, only the outermost spunbonded layer may be designed to be hydrophilic, or the whole top spunbonded layer may be designed to be hydrophilic.

In one embodiment of the present application, the weight of the hydrophilic spunbonded layer may account for 30% to 50% of the weight of the whole single sided hydrophilic nonwoven fabric. In the hydrophilic spunbonded layer, the diameter of the fibers may be between 10 μm and 30 μm, and preferably between 15 μm and 25 μm, and the average diameter of the fibers may be about 17-21 μm. In a preferred embodiment, the diameter of the fibers in the hydrophilic spunbonded layer may be between 15 μm and 25 μm, and the average diameter of the fibers may be about 19 μm.

In one embodiment of the present application, the weight of the hydrophobic spunbonded layer may account for 30% to 50% of the weight of the whole single sided hydrophilic nonwoven fabric. In the hydrophobic spunbonded layer, the diameter of the fibers may be between 10 μm and 30 μm, and preferably between 15 μm and 25 μm, and the average diameter of the fibers may be about 17-21 μm. In a preferred embodiment, the diameter of the fibers in the hydrophobic spunbonded layer may be between 15 μm and 25 μm, and the average diameter of the fibers may be about 19 μm.

Preferably, a hydrophilic masterbatch may be added to the top spunbonded layer to make it hydrophilic. The types of the hydrophilic masterbatch are not limited, as long as it can make the spunbonded layer hydrophilic without impairing the physical properties of the spunbonded layer. In a preferred embodiment, the hydrophilic master batch may be, for example, a glyceride of fatty acids. Examples of glycerides of fatty acids may include, but are not limited to, tributyrin, tricaprylin, myristin, and glycerol 2-ethylcaproate, etc. In one embodiment, the hydrophilic masterbatch may be added in an amount of from 1 wt % to 10 wt %, preferably from 1 wt % to 5 wt %, and more preferably from 2 wt % to 5 wt %, based on the total weight of the spunbonded fibers for the hydrophilic spunbonded layer.

Since one side of the single sided hydrophilic nonwoven fabric of the present application is hydrophilic, the condensed water may be absorbed after steam sterilization. In one embodiment, the water absorption capacity of the single sided hydrophilic nonwoven fabric, as determined in accordance with GB/T 1540 method, may be from 10 $g/m^2$ to 30 $g/m^2$, for example, from 15 $g/m^2$ to 25 $g/m^2$.

The single sided hydrophilic nonwoven fabric of the present application further comprises a middle meltblown layer located between the top spunbonded layer and the bottom spunbonded layer. The single sided hydrophilic nonwoven fabric may contain 5 wt % to 40 wt % of meltblown fibers, which will provide high barrier properties to prevent the penetration of microorganisms and bacteria. For example, the weight of the middle meltblown layer can account for 10% to 30% of the weight of the whole single sided hydrophilic nonwoven fabric.

When the content of meltblown fibers contained in the single sided hydrophilic nonwoven fabric is less than 5 wt %, sufficient barrier properties may not be provided, and when the content of meltblown fibers is more than 40 wt %, the tensile strength of the obtained nonwoven fabric may be insufficient.

Referring to FIG. 1, which shows a schematic view of the single sided hydrophilic nonwoven fabric according to a preferred embodiment of the present application.

As shown in FIG. 1, the single sided hydrophilic nonwoven fabric according to the present application sequentially includes a top spunbonded layer, a middle meltblown layer and a bottom spunbonded layer from top to bottom.

In the embodiment shown in FIG. 1, the top spunbonded layer may be designed to be a hydrophilic spunbonded layer. In this top spunbonded layer, the diameter of the fibers may be 15 μm to 25 μm, and the average diameter of the fibers may be about 19 μm. The top spunbonded layer may absorb 10 $g/m^2$ to 30 $g/m^2$ of condensed water. In addition, the weight of the top spunbonded layer may account for 30% to 50% of the weight of the whole nonwoven fabric. As an inner layer in the CSR wrap, this top spunbonded layer can absorb condensed water after steam sterilization due to its hydrophilicity, thus avoiding the occurrence of wet packs problems.

The bottom spunbonded layer may be designed to be a hydrophobic spunbonded layer. In this bottom spunbonded layer, the diameter of the fibers may be from 15 μm to 25 μm, and the average diameter of the fibers may be about 19 μm. In addition, the weight of the bottom spunbonded layer may account for 30% to 50% of the weight of the whole nonwoven fabric.

The middle meltblown layer located between the top spunbonded layer and the bottom spunbonded layer is also hydrophobic. In the middle meltblown layer, the diameter of the fibers may range from 0.5 μm to 10 μm, and the average diameter of the fibers may be about 2 μm. In addition, the weight of the bottom spunbonded layer may account for 30% to 50% of the weight of the whole nonwoven fabric.

The single sided hydrophilic nonwoven fabric of the present application comprises both a top spunbonded layer and a bottom spunbonded layer, wherein the spunbonded fibers may account for 60 wt % to 95 wt % of the weight of the single sided hydrophilic nonwoven fabric, thereby providing sufficient tensile strength to accommodate medical devices.

In addition, since both the middle meltblown layer and the bottom spunbonded layer are hydrophobic, they can provide an effective barrier to prevent the penetration of bacteria.

Figure 2:
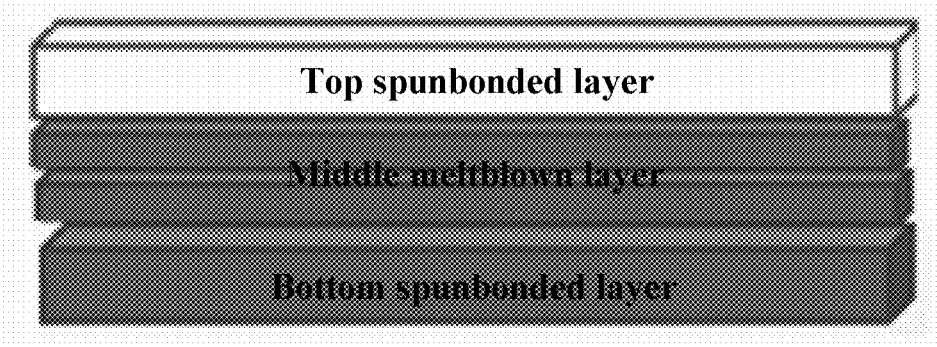
FIG. 2 is a schematic view of the single sided hydrophilic nonwoven fabric according to another preferred embodiment of the present application.

FIG. 2 is a schematic view of the single sided hydrophilic nonwoven fabric according to another preferred embodiment of the present application. As shown in FIG. 2, the single sided hydrophilic nonwoven fabric differs from the single sided hydrophilic nonwoven fabric shown in FIG. 1 only in that its middle meltblown layer is composed of two meltblown layers.

The manufacture of the nonwoven fabrics with SMS structure is known in the art, wherein the spunbonded and meltblown equipment or beams are used in combination, and the formed fiber layer is consolidated by thermal bonding consolidation technology. For example, for a nonwoven fabric with the structure shown in FIG. 1, a spunbonded bottom layer may be formed from spunbonded fibers in the No. 1 beam, and the fibers may be meltblown onto the bottom spunbonded layer in the No. 2 beam, and then another layer of spunbonded fibers may be spread on the meltblown layer in the No. 3 beam. After that, the resulting multilayer structure may be bonded and consolidated by calendering, thereby obtaining a nonwoven fabric with SMS structure.

In particular, the single sided hydrophilic nonwoven fabric according to the present application has high tensile strength, and one side thereof is hydrophilic and the other side is hydrophobic, and the benefits it can achieve include, but are not limited to:

Hydrophilic spunbonded layer absorbs the condensed water after steam sterilization Hydrophobic meltblown and spunbonded layers provide a barrier to prevent the penetration of bacteria High tensile strength may decrease the possibility of damage to the wrap According to another aspect of the present application, there is also provided a sterilized CSR wrap formed by the above single sided hydrophilic nonwoven fabric, which has the following characteristics, including but not limited to:

Allow sterilizing agents to penetrate

Allow air to penetrate

9

Allow to load a given weight of medical devices without breaking

Allow to absorb a given weight of condensed water

Resistance to microbial pass-through

Resistance to water penetration

Wear resistance

The single sided hydrophilic CSR wrap according to the present application may be used as sterilization packaging for medical devices. CSR wrap are designed to be used by utilizing the following sterilization methods: Steam sterilization, EO sterilization, Hydrogen peroxide sterilization, and Formaldehyde sterilization. CSR wrap are designed and manufactured to meet EN 868.2 standard—Packaging for terminally sterilized medical devices, Section 2: sterilization wrap-requirements and test methods, and YY/T 0698.2 standard—Packaging materials for terminal sterilized medical devices, Section 2: sterilized wrapping materials-requirements and test methods.

Examples

Hereinafter, preferred embodiments will be provided to better understand the present invention. However, the following examples are only for illustrative purposes and for a better understanding of the present disclosure by those skilled in the art. Trade names sold by corresponding chemical companies may be presented in the following examples. According to the teachings of the present invention, the corresponding components or products can be obtained by those skilled in the art through purchasing approaches based on the names of the commercial chemicals provided. In addition, the corresponding components can be also synthesized or manufactured by those skilled in the art based on the teachings of the present invention. Therefore, the present invention should not be limited by these examples.

Example 1

Raw Materials:

Polypropylene resin 3155E5 used in spunbonded process has an MFR of 35 g/10 min;

Polypropylene resin HP461Y used in meltblown process has an MFR of 1400 g/10 min;

Hydrophilic masterbatch MB-4031-TS, with an MFR of 550 g/10 min, was only added to the top spunbonded layer at the level of 3%;

Blue masterbatches PCB377BN and PCB377CN, added to the middle meltblown layer and the bottom spunbonded layer, wherein PCB377BN and PCB377CN was added in an amount of 1.5% and 6.5%, respectively;

Tensile enhancer TE 1096, added to both the top spunbonded layer and the bottom spunbonded layer, and was added in an amount of 3%;

A laminate with S-M-M-S structure was obtained by using the above raw materials in accordance with the spunbonded-meltblown-meltblown-spunbonded process, and the laminate with S-M-M-S structure was consolidated by calendering, thereby obtaining an S-M-M-S wrapping material, which is Whi #BL15 S-M-M-S with a basis weight of 60 gsm.

1. Physical Characteristics of S-M-M-S Wrapping Materials

Physical properties of S-M-M-S wrapping materials, including basis weight, tensile strength, elongation and tearing resistance in the longitudinal direction (i.e., machine direction, MD), tensile strength, elongation and tearing resistance in the transverse direction (i.e., cross direction, CD), bursting strength, air permeability, hydrostatic pressure (HSH) and water absorption capacity, were measured in accordance with the testing methods listed in Table 1 below. The results are shown in Table 1 below.

TABLE 1

| Characteristic | Unit | Test Method | Average | EN868-2 Requirement | conformity |
|---|---|---|---|---|---|
| Basis Weight | g/m$^2$ | EN ISO 536 | 60.4 (+0.6%) | with in ±5% | Pass |
| Tensile Strength-MD | KN/m | EN ISO 1924-2 | 3.2 | not less than 1 KN/m | Pass |
| Elongation-MD | % | EN ISO 1924-2 | 89.92 | not less than 5% | Pass |
| Tensile Strength-CD | KN/m | EN ISO 1924-2 | 1.82 | not less than 0.65 KN/m | Pass |
| Elongation-CD | % | EN ISO 1924-2 | 84.2 | not less than 7% | Pass |
| Tearing Resistance-MD | mN | EN ISO 1974 | 5233 | not less than 750 mN | Pass |
| Tearing Resistance-CD | mN | EN ISO 1974 | 11929 | not less than 1000 mN | Pass |
| Bursting Strength | Kpa | EN ISO 2758 | 314 | not less than 130 kPa | Pass |
| Air Permeability | L/min/100 cm$^2$ | ASTM D 737 | 119.4 | N/A | N/A |
| HSH | mbar | EN20811 | 55.08 | N/A | N/A |
| Water Absorption Capacity | g/m$^2$ | GB/T 1540 | 19.87 | N/A | N/A |

2. Determination of Microbial Barrier

In order to show compliance to ISO 11607-1:2019-02, Section 5.1.6 a) "microbial barrier", the above materials were examined according to ISO 11607-1:2019-02, Section 5.2.3 test method DIN 58953-6:2016-12, Section 3 (germ proofness test under humidity) and Section 4 (germ proofness test with air permeance).

2.1 Determination of Germ Proofness Under Humidity

A sample material was examined according to DIN 58953-6, Section 3, wherein both sides (side A and side B) of the sample material were contaminated with the test germ, and each was sterilized by steam at 134° C. for 4 minutes. The results are shown in Table 2 below.

TABLE 2

| Sterilization -- | Number of CFU/agar plate | | | | | |
|---|---|---|---|---|---|---|
| Test side | 1 | 2 | 3 | 4 | 5 | Σ |
| Steam 134° C. Side A | 0 | 0 | 0 | 0 | 0 | 0 |
| Steam 134° C. Side B | 0 | 0 | 0 | 0 | 0 | 0 |

CFU = colony forming unit 2.2 Determination of Germ Proofness with Air Permeance A sample material was examined according to DIN 58953-6, Section 4, in which both sides (side A and side B) of the sample material were contaminated with the test germ, and each was sterilized by steam at 134° C. for 4 min. The results are shown in Table 3 below.

TABLE 3

| Sterilization -- | Number of CFU/Specimem | | | | | | | | | | |
|---|---|---|---|---|---|---|---|---|---|---|---|
| Test side | 1 | 2 | 3 | 4 | 5 | 6 | 7 | 8 | 9 | 10 | Σ |
| Steam 134° C. Side A | 0 | 0 | 0 | 0 | 0 | 0 | 0 | 0 | 0 | 0 | 0 |
| Steam 134° C. Side B | 0 | 0 | 0 | 0 | 0 | 0 | 0 | 0 | 0 | 0 | 0 |

The evaluation of microbial barrier was conducted.

The germ proofness under humidity and air permeance of the sample material were examined after sterilization by steam (134° C./4 min). The results show that the S-M-M-S wrapping material has sufficient barrier for germ proof according to DIN 58953-6, Section 3.8 and Section 4.8.6.

3. Stability Testing

The stability testing was used to demonstrate that the sterile barrier system maintains integrity over time per ISO 11607-1:2019. Following accelerated aging test, protocols were used with reference of ASTM F1980-21, with a temperature of 65° C. and a relative humidity of 80%±5%. The accelerated aging time (7 days) is equivalent to the real aging time (180 days) under room temperature condition. The results are shown in Table 4 below.

TABLE 4

| Test Group | The Growth of Microorganisms (Growth/Test tube) | | |
|---|---|---|---|
| | Aerobe | Anaerobion | Fungus |
| Pre-sterilization control group | 5/5 | 5/5 | 5/5 |
| After sterilization before storage | 0/5 | 0/5 | 0/5 |
| After sterilization stored 7 days | 0/5 | 0/5 | 0/5 |

The sample material was able to maintain package sterility for 180 days under controlled environmental conditions during the accelerated aging test.

Although the exemplary embodiments of the present application have been described in detail, the scope of the present application is not limited thereto. Various modifications and improvements made by those skilled in the art through adopting the basic concept of the present application as defined in the claims also fall within the scope of the present application.

The invention claimed is:

1. A single sided hydrophilic nonwoven fabric, having a structure comprising (i) a top spunbonded layer including one or more spunbond layers, (ii) a middle meltblown layer including one or more meltblown layers, and (iii) a bottom spunbonded layer including one or more spunbond layers, wherein one side of the nonwoven fabric is hydrophilic and the other side thereof is hydrophobic; and wherein the top spunbond layer and/or the bottom spunbond layer include tensile enhancer that increases the crystallization percentage of the top spunbond layer and/or the bottom spunbonded layer, wherein the tensile enhancer is added in an amount of from 1 wt % to 10 wt %, based on the total weight of the top spunbonded layer and/or the bottom spunbonded layer; and wherein the single sided hydrophilic nonwoven fabric has (a) a longitudinal tensile strength, as determined in accordance with EN ISO 1924-2, in the range of 1.2 KN/m to 5.0 KN/m; and (b) a transverse tensile strength, as determined in accordance with EN ISO 1924-2, in the range of 1.2 KN/m to 5 KN/m wherein the single sided hydrophilic non nonwoven fabric has a basis weight from 40 to 80 gsm, and a water absorption capacity, as determined in accordance with the GB/T 1540 method, is from 10 g/m$^2$ to 30 g/m$^2$.

2. The single sided hydrophilic nonwoven fabric according to claim 1, wherein the single sided hydrophilic nonwoven fabric comprises (i) 60 wt % to 95 wt % of spunbonded fibers, (ii) 5 wt % to 40 wt % of meltblown fibers, or (iii) both (i) and (ii).

3. The single sided hydrophilic nonwoven fabric according to claim 1, wherein the middle meltblown layer is composed of two meltblown layers.

4. The single sided hydrophilic nonwoven fabric according to claim 1, wherein the middle meltblown layer accounts for 10% to 30% of the weight of the whole single sided hydrophilic nonwoven fabric.

5. The single sided hydrophilic nonwoven fabric according to claim 4, wherein the middle meltblown layer has meltblown fibers having a diameter between 0.5 μm and 10 μm.

6. The single sided hydrophilic nonwoven fabric according to claim 1, wherein the top spunbonded layer is a hydrophilic spunbonded layer, and the bottom spunbonded layer is a hydrophobic spunbonded layer.

7. The single sided hydrophilic nonwoven fabric according to claim 6, wherein the weight of the hydrophilic spunbonded layer accounts for 30% to 50% of the weight of the whole single sided hydrophilic nonwoven fabric.

8. The single sided hydrophilic nonwoven fabric according to claim 6, wherein the weight of the hydrophobic spunbonded layer accounts for 30% to 50% of the weight of the whole single sided hydrophilic nonwoven fabric.

9. The single sided hydrophilic nonwoven fabric according to claim 6, wherein a hydrophilic masterbatch is added to the top spunbonded layer.

10. The single sided hydrophilic nonwoven fabric according to claim 9, wherein the hydrophilic masterbatch is a glyceride of fatty acid.

11. The single sided hydrophilic nonwoven fabric according to claim 9, wherein the hydrophilic masterbatch is added in an amount of from 1 wt % to 10 wt %, based on the total weight of the top spunbonded layer.

12. The single sided hydrophilic nonwoven fabric according to claim 1, wherein a longitudinal tensile strength of the single sided hydrophilic nonwoven fabric, as determined in accordance with EN ISO 1924-2, is in the range of 2 KN/m to 5.0 KN/m.

13. The single sided hydrophilic nonwoven fabric according to claim 1, wherein a longitudinal elongation of the single sided hydrophilic nonwoven fabric, as determined in accordance with EN ISO 1924-2, is in the range of 50% to 120%.

14. The single sided hydrophilic nonwoven fabric according to claim 1, wherein a transverse tensile strength of the single sided hydrophilic nonwoven fabric, as determined in accordance with EN ISO 1924-2, is in the range of 1.5 KN/m to 3.5 KN/m.

15. The single sided hydrophilic nonwoven fabric according to claim 1, wherein a transverse elongation of the single sided hydrophilic nonwoven fabric, as determined in accordance with EN ISO 1924-2, is in the range of 50% to 150%.

16. The single sided hydrophilic nonwoven fabric according to claim 1, wherein the single sided hydrophilic nonwoven fabric has a microbial barrier of the single sided hydrophilic nonwoven fabric, as determined in accordance with EN868, that is maintained for 180 days or longer.

17. A central supply room (CSR) wrap made from the single sided hydrophilic nonwoven fabric according to claim 1.

18. A method of sterilizing a medical device, comprising: (i) enclosing the medical device within a central supply room (CSR) wrap comprising a single sided hydrophilic nonwoven fabric according to claim 1 to provide an enclosed medical device, and (ii) subjecting the enclosed medical device to a steam sterilization operation.

* * * * *